United States Patent [19]

Kanezaki

[11] 4,028,340
[45] June 7, 1977

[54] PROCESS FOR PREPARING P-VINYLPHENOL POLYMER

[75] Inventor: Kenji Kanezaki, Kitakyushu, Japan

[73] Assignee: Maruzen Oil Co. Ltd., Osaka, Japan

[22] Filed: Feb. 27, 1976

[21] Appl. No.: 661,874

[30] Foreign Application Priority Data

Mar. 1, 1975 Japan .............................. 50-25207

[52] U.S. Cl. ...................... 260/47 UA; 260/47 UP; 526/75; 528/491; 528/497; 528/498; 528/501

[51] Int. Cl.$^2$ .............. C08F 132/00; C08F 112/00; C08F 12/04

[58] Field of Search .................... 260/47 UA, 47 UP

[56] References Cited

UNITED STATES PATENTS

| | | | |
|---|---|---|---|
| 2,006,517 | 7/1933 | Seymour | 260/47 UA |
| 2,583,638 | 1/1952 | Evans et al. | 260/47 UA |
| 2,694,693 | 11/1954 | Minsk | 260/47 UA |
| 2,698,863 | 11/1955 | Dickey | 260/47 UA |
| 2,700,029 | 1/1955 | Cassidy | 260/47 UA |
| 3,826,784 | 7/1974 | Satomura | 260/47 UA |

FOREIGN PATENTS OR APPLICATIONS 903,062   12/1959   United Kingdom .......... 260/47 UP

OTHER PUBLICATIONS

Journal Organic Chemistry, vol. 23, Apr. 1958, pp. 544–549.

*Primary Examiner*—Joseph L. Schofer
*Assistant Examiner*—Herbert J. Lilling
*Attorney, Agent, or Firm*—Sughrue, Rothwell, Mion, Zinn & Macpeak

[57] ABSTRACT

A process for preparing a high purity p-vinylphenol polymer which comprises dehydrogenating crude p-ethylphenol containing at least one of m-ethylphenol and o-ethylphenol to convert the ethylphenol(s) to vinylphenol(s), polymerizing the resulting crude product without removing the o- and/or m-vinylphenols, and purifying the resulting polymerization product.

18 Claims, No Drawings

PROCESS FOR PREPARING P-VINYLPHENOL POLYMER

BACKGROUND OF THE INVENTION

1. FIELD OF THE INVENTION

This invention relates to an economically advantageous process for preparing a high purity p-vinylphenol polymer from crude p-ethylphenol in fewer steps.

2. DESCRIPTION OF THE PRIOR ART

It has been difficult to obtain high purity p-vinylphenol polymer; in fact, no commercial production is now practiced. According to conventional polymer production techniques, high purity p-vinylphenol polymer can generally be prepared as follows: First, crude p-ethylphenol is purified to form high purity p-ethylphenol. This step is required in order to remove m-ethylphenol and o-ethylphenol inevitably formed in producing crude p-ethylphenol. For example, in the productin of p-ethylphenol by sulfonating ethylbenzene and then subjecting the resulting product to alkali fusion, i.e., reaction of the resulting product with an alkali hydroxide in the fused state, the resulting crude p-ethylphenol contains about 5% (unless otherwise specified, all percentages in the specification are by weight) m-ethylphenol, about 5% o-ethyl-phenol, and some amounts of impurities such as phenol or cresol. The resulting high purity p-ethylphenol is then dehydrogenated to p-vinylphenol. The crude vinylphenol obtained contains phenols (phenols other than p-vinylphenol) such as unreacted p-ethylphenol, phenol or cresol, water and p-vinylphenol oligomers or low molecular weight polymers in addition to p-vinylphenol. The composition of the crude vinylphenol obtained by dehydrogenation varies greatly according to the dehydrogenation conditions. One example of the composition of the crude p-vinylphenol is 46.0% p-ethylphenol, 15.4% p-vinylphenol, 1.2% other phenols, 5.0% water, 0.6% p-vinylphenol oligomers or low molecular weight polymers, and 31.8% benzene. The benzene is generally introduced in the dehydrogenating step as a reaction diluent, but its use is not mandatory.

According to conventional polymerization methods, the crude vinylphenol is subjected to a purification step to separate purified p-vinylphenol.

p-Vinylphenol is a very unstable monomer, and it is very difficult, if not impossible, to purify and separate p-vinylphenol, partly because no suitable polymerization inhibitor for p-vinylphenol has been found. Such purification and separation are also very expensive.

The purified p-vinylphenol separated is then polymerized, and the desired polymer is separated from the polymerization product and purified. In other words, according to conventional techniques of preparing polymers, the preparation of a high purity p-vinylphenol polymer requires a number of steps comprising purifying crude p-ethylphenol, dehydrogenating the purified p-ethylphenol, purifying the crude p-vinylphenol obtained from the dehydrogenating, polymerizing the purified p-vinylphenol, and separating the polymer from the polymerization and purifying it. Furthermore, since the above method includes the steps of purifying the crude p-ethylphenol and the crude p-vinylphenol, which are complicated and very difficult, it is disadvantageous from the standpoint of cost.

SUMMARY OF THE INVENTION

It is one object of this invention to provide a process for producing a p-vinylphenol polymer of high purity.

Another object of this invention is to provide a process for preparing a p-vinylphenol polymer of high purity in an economical and simple manner by a process which comprises fewer steps than conventional processes.

As a result of our investigations in order to achieve the above objects, we found that among the vinylphenol isomers, the para-isomer is more easily polymerizable than the meta and ortho-isomers, and even when the para-isomer containing the meta- and ortho-isomers is polymerized, the highly polymerized portion of the resulting polymerization product consists almost solely of a polymer of the para-isomer, and most of the metaisomer and ortho-isomer are present in the unreacted portion or the low polymerized portion, and that when the crude p-vinylphenol obtained by the dehydrogenation of p-ethylphenol and containing phenols other than vinylphenol such as unreacted p-ethylphenol, cresol or phenol is polymerized as such, substantially only a p-vinylphenol polymer can be obtained. This finding finally led to the discovery that a p-vinylphenol polymer having a high purity such as to be feasible for practical use can be obtained by dehydrogenating crude p-ethylphenol directly, polymerizing the resulting crude p-vinylphenol without purification, and purifying the resulting polymerization product.

Accordingly, the present invention provides a process for preparing a high purity p-vinylphenol polymer, which comprises dehydrogenating crude p-ethylphenol containing at least one of m-ethylphenol and o-ethylphenol to convert the ethylphenols to vinylphenols, polymerizing the resulting crude dehydrogenation product as such, and purifying the resulting polymerization product.

DETAILED DESCRIPTION OF THE INVENTION

The crude p-ethylphenol used in this invention contains at least one of m-ethylphenol and o-ethylphenol, its isomers, in arbitrary amounts, i.e., the amount is optional and is not specifically limited. Even when this isomeric mixture consists of, for example, 5 parts by weight of p-ethylphenol and 95 parts by weight of the above isomers, it can be used in the process of this invention. However, the amounts of the isomers are preferably as small as possible, and, generally, when the amounts of the isomer(s) are not more than about 50 parts by weight per 50 parts by weight of crude p-ethylphenol, polymers of the isomers do not substantially mix in the final polymer. The amounts of the isomer(s) also differ according to the conditions for preparing p-ethylphenol. Generally, it is easy to produce crude p-ethylphenol containing the isomers in amounts of about 10 to about 15 parts by weight per 100 parts by weight of p-ethylphenol. Hence, it is seldom ever necessary to use crude p-ethylphenol which contains the isomers in an extremely large amount as exemplified above.

Furthermore, the crude p-ethylphenol used in this invention may be one produced by any method. It may contain unreacted compounds, by-products, and impurities such as phenol or cresol in addition to the above isomers.

One example of preparing crude p-ethylphenol comprises sulfonating ethylbenzene with sulfuric acid and subjecting the sulfonation product to alkali fusion (for details, see L. Sempotewsk, Ber. 22, 2662 (1889) or V. Denlofbn et al., J.A.C.S. 66, 118 (1944)). Even when the sulfonation in this process is carried out under conditions which will give the largest amount of a sulfonation product of p-ethylbenzene, for example, at a temperature of about 120° C, some amounts of sulfonation products of the meta-isomer and ortho-isomer form. For example, the crude p-ethylphenol obtained by this process consists of about 64 to about 90.5% p-ethylphenol, about 4 to about 10% m-ethylphenol, about 4 to about 10% o-ethylphenol, about 1 to about 5% phenol, about 0.5 to about 3% cresol, and 0 to about 8% of other components. Crude p-ethylphenol of such a composition can be directly used in the process of the present invention.

In the conventional process for preparing crude p-ethylphenol, a modified procedure is sometimes employed which comprises preparing a sulfonation product containing a paraisomer in a concentrated state by utilizing the differences in properties among the sulfonation products of the para-, meta-, and ortho-isomers, as briefly described in P. B. Report 91355, and, for example, subjecting the product to a crystallization separating method whereby only the para-isomer is crystallized while the meta- and ortho-isomers are maintained liquid, and the crystals of the para-isomer are separated by filtration, and subjecting the resulting sulfonation product to alkali fusion. The crude p-ethylphenol prepared by such a procedure, for example, consists of about 90 to about 98% p-ethylphenol, about 0.4 to about 1% m-ethylphenol, about 0.4 to about 1% o-ethylphenol, about 0.5 to about 1.5% phenol, about 0.5 to about 1.5% cresol, and 0 to about 5% of other components. Crude p-ethylphenol of such a composition can also be used in the present invention.

When the above alkali fusion product is distilled by a simple distillation procedure without using a fractionating column including a large number of trays, for example, by a simple distillation device to thereby separate readily removable by-products such as cresol or phenol having a boiling point of not more than about 200° C, there can be obtained crude p-ethylphenol consisting of about 97 to about 99% p-ethylphenol, about 0.4 to about 1% m-ethylphenol, about 0.4 to about 1% o-ethylphenol, 0 to about 0.1% phenol, 0 to about 0.1% cresol, and 0 to about 0.2% of other components. Such a crude p-ethylphenol can also be used in the present invention.

Since o-ethylphenol (b.p. about 208° C) is relatively easily separable from p-ethylphenol (b.p. 218° C) by distillation, it may be separated, if desired, from the crude p-ethylphenol prior to use. As a result of this separation, there is obtained crude p-ethylphenol consisting of about 98 to about 99.5% p-ethylphenol, about 0.4 to about 1% m-ethylphenol, about 0.1 to about 0.2% o-ethylphenol, 0 to about 0.01% phenyl, and 0% of cresol. Such a crude p-ethylphenol can also be used in the present invention.

p-Ethylphenol can also be prepared by reducing p-hydroxyacetophenone (see, for example, D. Noghtungale et al., J. Org. Chem., 14, 1089 (1949)), or by alkylating phenol with ethyl ether (for details, see Baddeley, J.C.S., 1944, 330).

Applicants have found, in fact, that, in general, if the content of m-ethylphenol and/or o-ethylphenol is about 0.4 to about 95% by weight, such a starting material can be processed with relative ease in accordance with the present invention.

In the process of this invention, crude p-ethylphenol as obtained from such processes of preparing p-ethylphenol or crude p-ethylphenol obtained by subjecting such a crude p-ethylphenol to a simple distillation procedure similar to that previously mentioned can be used.

In the process of this invention, the crude p-ethylphenol is directly fed to a dehydrogenation step, and dehydrogenated. The dehydrogenation can be performed by any known procedure under any reaction conditions which cause conversion of ethylphenol to vinylphenol. The reaction procedure and conditions are therefore not particularly limited (see, for example, Japanese Patent Publication No. 41183/74 and U.S. Pat. No. 3,418,381).

The dehydrogenation is carried out in the presence of a dehydrogenation catalyst, for example, an oxide of iron, zinc, magnesium, chromium, aluminum, vanadium, molybdenum, manganese, cobalt, nickel, copper, cadmium, antimony, tellurium or cerium, or mixtures at any desired ratio of at least two of these oxides which is/are generally dispersed in and supported on a carrier consisting of an oxide of an alkaline earth metal such as beryllium, magnesium, calcium, strontium or barium. Usually, the catalytic dehydrogenation is carried out at a reaction temperature of about 400° to about 700° C, preferably 450° to 650° C, most preferably 540° to 640° C, using a diluent in an amount of about 5 to about 20 mols per mol of ethylphenol with the liquid hourly space velocity (LHSV) of ethylphenol passing through the catalyst being maintained at about 0.1 to about 10 $hr^{-1}$, preferably 02. to 2.0 $hr^{-1}$, at a pressure of about 1/100 atm. to about 1 $kg/cm^2$, generally at atmospheric pressure. The diluent used may, for example, be water, low-boiling petroleum fractions such as petroleum ether, naphtha, etc., benzene, toluene, xylene, methane, ethane, propane, butane, hexane, or mixtures thereof.

When the catalytic dehydrogenation is carried out under the aforesaid conditions, the conversion of ethylphenols in the crude p-ethylphenol to vinylphenols is about 20 to about 70% (preferably 20 to 50% from the viewpoint of selectivity). Hence, the crude p-vinylphenol, the dehydrogenation reaction product, contains a fairly large amount of unreacted ethylphenols.

The crude p-vinylphenol obtained by dehydrogenation is directly polymerized without separating and purifying p-vinylphenol. If desired, crude p-ethylphenol may be added to the crude p-vinylphenol. This is because the molecular weight of the final p-vinylphenol polymer can be adjusted by adjusting the proportion of vinylphenol and other phenols in the crude p-vinylphenol resulting from the dehydrogenation. When the content of phenols other than vinylphenol in the crude p-vinylphenol increases, the molecular weight of the intended p-vinylphenol decreases. On the other hand, when the content of the other phenols decreases, the molecular weight of the p-vinylphenol polymer increases. If the polymerization of crude p-vinylphenol as prepared is likely to afford a p-vinylphenol polymer having a higher molecular weight than desired, the molecular weight of the p-vinylphenol polymer can be adjusted by adding crude p-ethylphenol to the starting crude p-vinylphenol.

Instead of the crude p-ethylphenol, other diluents can also be used, for example, phenols (all isomers are included) such as phenol, cresol, xylenol, ethylphenol, catechol, pyrogallol or hydroquinone, carbonyl containing compounds such as acetone, methyl ethyl ketone, methyl isobutyl ketone, cyclohexanone or acetophenone, sulfone containing compounds such as dimethyl sulfone, dibutyl sulfone or diphenyl sulfone, sulfoxide-containing compounds such as dimethyl sulfoxide, dibutyl sulfoxide or diphenyl sulfoxide, and nitro containing compounds such as nitromethane, nitropropane, nitrobenzene or nitrotoluene. Since these diluents must be separated when unreacted ethylphenol is recycled to the dehydrogenation step after removing the polymer from the polymerization reaction product, it is most preferred to use crude p-ethylphenol as a diluent.

Since it is also possible to adjust the content of ethylphenol in the crude p-vinylphenol by regulating the dehydrogenation conditions of the crude p-ethylphenol, the molecular weight of the p-vinylphenol polymer can also be adjusted by adjusting the dehydrogenation conditions. For example, when the dehydrogenation is carried out under mild conditions, the content of unreacted ethylphenols in the crude p-vinylphenol tends to increase. In such a case, the molecular weight of the p-vinylphenol polymer obtained by polymerizing such crude p-vinylphenol becomes lower.

Generally, crude p-vinylphenol is polymerized by a heat polymerization or cationic polymerization technique. The polymerization conditions are optional. Generally, in the case of the heat polymerization, the mol ratio of diluent (whether the diluent is crude p-ethylphenol or another diluent as earlier described) to p-vinylphenol is adjusted to about 0.05 to about 100, preferably 0.2 to 2, and the crude p-vinylphenol is conveniently heat polymerized at a temperature of about 60 to about 200° C, preferably about 80° to about 170° C, for a period of about 5 minutes to about 100 hours, generally, 5 minutes to 10 hours, and usually without adding a catalyst. When the polymerization is performed under these conditions, the resulting polymer has a weight average molecular weight of about 3,000 to about 12,000. When the polymerization conditions are outside the preferred ranges specified above, polymers having a weight average molecular weight of less than about 3,000 or larger than about 12,000 are also formed. The molecular weight of the polymer becomes higher with higher proportions of p-vinylphenol and lower polymerization temperatures. When the polymerization time is made longer, the conversion becomes higher, but this has no impact upon the molecular weight of the resulting polymer. Since the heat polymerization is not influenced by the pressure, the pressure employed can be optionally selected, for example, from reduced pressure to elevated pressure, and, in general, is suitably atmospheric pressure. Also, the crude p-vinylphenol may be set under reduced pressure before the polymerization for the purpose of removal of benzene or water which is a solvent in the dehydrogenation.

When the polymerization conditions are too severe, the polymerization of m- and o-vinylphenol is promoted, and the amounts of m- and o-vinylphenol polymers in the resulting p-vinylphenol polymer increase. Hence, the advantage of the present invention is reduced. Furthermore, in the polymerization, the molecular weight of the desired p-vinylphenol polymer can be adjusted easily and with good reproducibility by properly choosing the polymerization reaction conditions. For example, when the polymerization temperature is set high or crude p-vinylphenol having a low p-vinylphenol content is used, a p-vinylphenol polymer having a low polymerization degree is obtained. On the other hand, when the polymerization temperature is set low or crude p-vinylphenol having a high p-vinylphenol content is used, a p-vinylphenol polymer having a high polymerization degree is obtained.

The p-vinylphenol polymer can also be obtained by cationically polymerizing the crude p-vinylphenol. The polymerization conditions are optional. Generally, the polymerization is carried out at a temperature of about 30° to about -80° C using a Friedel-Crafts catalyst such as halides of boron, antimony, iron, tellurium, tin, titanium, bismuth and zinc, preferably $BF_3$ or $AlCl_3$, a sulfuric acid, hydrofluoric acid, phosphoric acid, phosphorus pentoxide or hydrochloric acid catalyst, in an amount of about 0.001 to about 0.1 mol per mol of the p-vinylphenol. A diluent, such as chloroform, carbon tetrachloride, dichloroethane, trichloroethylene, pentane, hexane, octane, decane, petroleum ether, benzene, toluene, xylene, cyclohexane or methylcyclohexane, can be used in an amount of up to about 1,000% by weight based on the crude p-vinylphenol. The reaction sometimes proceeds instantaneously, or sometimes takes 5 hours or more. For example, when the polymerization is carried out at room temperature using a Friedel-Crafts catalyst such as $BF_3$, the polymerization reaction is completed within several minutes. Further, when the polymerization is carried out at room temperature using an acid catalyst such as HCl, several hours is required for completion of the polymerization reaction.

In the case of cationic polymerization, the catalyst must be removed from the polymerization product. The heat polymerization generally does not require catalysts, and so there is no need to remove them. From the standpoint of the simplicity of process steps, the heat polymerization technique is preferred. In other respects, these two polymerization techniques exhibit much the same results in the present invention.

The polymerization reaction product from the polymerization step is then subjected to a purification treatment. There is no particular limitation on specific procedures of the purification treatment. Preferably, however, the purification is performed by distillation or by precipitating the polymer using a non-solvent for the polymer.

The purification treatment by distillation can be carried out by any desired distillation procedure. However, a film evaporation method is preferable to a simple distillation method as will be described below.

When an attempt is made to separate phenols other than vinylphenol, unreacted vinylphenols, vinylphenol oligomers and other by-products from the polymerization reaction product by a "simple distillation procedure", the distillation bottoms becomes increasingly viscous with the concentration of the polymerization product, and the other phenols, the unreacted vinylphenol monomers or vinylphenol oligomers do not evaporate since they finally reach a caramelized state, i.e., a highly viscous state. This tends to obstruct the transmission of heat. It is usually very difficult to reduce the amounts of the above impurities present in the resulting polymer to not more than about 2 to about 5% by weight. When the temperature of the distillation bottoms is raised in order to reduce their viscosity, decomposition of the desired polymer takes place.

According to the film evaporation method, the heating time can be short, and therefore, even when high temperatures are employed, the decomposition of the polymer is inhibited. Furthermore, bubbling of the polymerization reaction product can be prevented by the wiper of the film evaporator. In the processes according to the present invention, the film evaporator used is not unduly limited. For example, conventional film evaporators produced by Luwa Co. or Sambay Co., both of Japan, are suitably used. Accordingly, the phenols other than vinylphenols, the unreacted vinylphenols containing m-and o-vinylphenols in the concentrated state, and the vinylphenol oligomers can be continuously removed from the polymerization reaction product with good efficiency, and thus, a p-vinylphenol polymer of high purity can be obtained easily.

Usually, the polymerization reaction product contains ethylphenol in an amount sufficient to dissolve the polymer, e.g., from about 95 to about 5%, preferably 90 to 50% by weight, and heating the polymerization product generally to a temperature of not more than about 80° C can give a uniform solution having a low viscosity which permits the feeding of the product to a film evaporator. Hence, the polymerization reaction product can be easily and simply fed to the film evaporator, and the resulting polymer does not undergo any thermal change. The film evaporation which is employed in the present invention is generally carried out at a pressure of less than about 20 mmHg, preferably less than 10 mmHg and at a temperature of from about 240° to about 300° C, preferably 240° to 280° C. In the above, the residence time of the polymerization product in the distillation region is generally from about 2 to about 10 seconds, preferably 2 to 4 seconds.

The method of purifying the polymerization reaction product by precipitating the desired polymer with a non-solvent for the polymer (to be referred to simply as a "non-solvent") will not be described.

The non-solvent used in this purifying method is one which does not dissolve the p-vinylphenol polymer but well dissolves vinylphenol monomers, low molecular weight (e.g., about 240 to about 500, preferably 240 to 360) polymers such as oligomers, ethylphenol, and other phenols. Suitable non-solvents are selected from hydrocarbons, halogenated hydrocarbons, and mixtures thereof. Examples of the hydrocarbons are aromatic hydrocarbons such as benzene, toluene, or xylene, aliphatic hydrocarbons such as n-pentane, i-pentane, n-hexane, i-hexane, n-octane or i-octane, and alicyclic hydrocarbons such as cyclopentane, cyclohexane, cycloheptane or cyclooctane. Examples of the halogenated hydrocarbons include chlorobenzene, chlorotoluene, chloropentane, chlorohexane, chloroheptane, chlorocyclopentane, chlorocyclohexane, bromobenzene, bromotoluene, bromopentane, bromohexane, bromoheptane, bromocyclopentane, and bromocyclohexane.

In the performance of this purifying method, it is generally preferred to add the polymerization reaction product to such a non-solvent as described above. The non-solvent is used in an amount of at least about 10 times, preferably 15 to 20 times, the volume of the polymerization reaction product. Prior to adding the polymerization reaction product to the non-solvent, it is preferred to heat the polymerization reaction product to form a uniform solution.

Suitably, the polymerization product is added either dropwise or by jetting it into the non-solvent. After adding the polymerization product to the non-solvent, the mixture is vigorously stirred in order to ensure sufficient contact between the polymerization product and the non-solvent and to thereby precipitate the polymer. The polymer precipitated is then separated by a conventional solid-liquid separating method such as filtration at reduced or elevated pressure, or by centrifugal separation. The polymer cake so separated is washed with the above non-solvent either batchwise or continuously to remove the unreacted vinylphenol monomers, low molecular weight polymers such as oligomers, ethylphenols and other phenols to afford a purified p-vinylphenol polymer as a final product. The washing conditions are not overly important and can be easily selected by one skilled in the art. In general, the washing is carried out at room temperature using a non-solvent in an amount of about 3 to about 20, preferably 5 to 20, times the weight of polymer cake, for economical purposes. When the polymerization reaction product is purified by recrystallization, the polymerization product first, in general, is dissolved in a solvent and then a non-solvent is added to the resulting solution followed by precipitating the polymer. On the other hand, according to the present invention, the polymerization reaction product can be obtained in the form of solution containing ethylphenol. Therefore, in a purification wherein a non-solvent for such a polymerization reaction product is employed, the addition of a solvent (a third substance) for dissolving the polymer is not required.

However, in the purification of this polymer, a third substance, which is a good solvent for the polymer, for example, a polar solvent such as acetone, methanol, methyl ethyl ketone or dimethyl formamide can, if desired, be added to the polymerization reaction product in an amount of about 5 to about 1,000% by weight to the p-vinylphenol polymer to form a uniform solution of the polymerization product which is subjected to the former-mentioned film evaporation or the latter-mentioned method of adding the non-solvent thereto to precipitate the polymer.

The polymer so obtained is a high purity p-vinylphenol polymer consisting essentially of p-vinylphenol units and being substantially free from m-vinylphenol units and o-vinylphenol units. The m- and o-vinylphenols that have come into the polymerization step together with p-vinylphenol are almost entirely concentrated in the unreacted compounds or low molecular weight polymerization products such as oligomers and removed as such. The purity of the p-vinylphenol polymer is generally at least about 95%, and can be increased easily to at least 98%.

Since the p-vinylphenol polymer obtained by the process of this invention is of such a high purity as mentioned above and has very superior physical and chemical properties, it finds a wide range of utility, for example, as a thermally stable resin, photosensitive resin, antistatic agent, static treating agent, ultrafiltration membrane, ion exchange membrane, or water treating agent. Low purity p-vinylphenol polymers containing large amounts of m- and o-vinylphenols are disadvantageous in end uses because of their unsatisfactory chemical properties.

The process of this invention does not require a step of purifying crude p-ethylphenol and a step of purifying crude p-vinylphenol which the prior art has considered as essential, and makes it possible to obtain a high purity p-vinylphenol polymer having equivalent utility to those obtained by the conventional techniques but more easily and economically and in fewer process steps than in the conventional methods.

Furthermore, according to the process of this invention, the molecular weight of the desired p-vinylphenol polymer can be adjusted easily and with good reproducibility by the simple procedure described in detail hereinabove.

The following Examples illustrate the process of this invention more specifically. It should be noted that these Examples are merely for illustrative purposes, and do not in any way limit the scope of the invention. All percentages in these Examples are by weight unless otherwise specified. The pressure employed in the Examples was atmospheric pressure unless otherwise indicated.

EXAMPLE 1

Crude ethylphenol consisting of 2.6% phenol and m- and p-cresols, 1.2% o-ethylphenol, 9.4% m-ethylphenol, and 86.8% p-ethylphenol was dissolved in benzene. The resulting solution was then passed through an iron oxide catalyst with vapor at 570° C and at an LHSV of p-ethylphenol (hereafter the same) of 1.0 hr$^{-1}$ under atmospheric pressure. The iron oxide catalyst was prepared by adding 9.5 parts by weight of magnesium oxide to an aqueous solution obtained by dissolving 7 parts by weight of ferric oxide in 180 parts by weight of water, stirring for 3 hours to form a precipitate, filtering the precipitate, washing with water, drying, sintering in air at 650° C for 3 hours and stamp molding. The molar ratio of ethylphenol/benzene/water was about 1/1/10. The resulting dehydrogenated product was allowed to stand at room temperature followed by separating the water. The crude vinylphenol so separated consisted of 31.8% benzene, 1.2% phenol and m- and p-cresols, 0.6% o-ethylphenol, 4.4% m-ethylphenol, 41.0% p-ethylphenol, 12.4% p-vinylphenol, 0.3% o-vinylphenol, 2.7% m-vinylphenol, 0.6% oligomers of vinylphenols, and 5.0% water. The molar ratio of the vinylphenols to the ethylphenols was 0.34.

The crude vinylphenol was directly placed in a three necked glass reactor equipped with a stirrer, and heat polymerized at 115° C for 8 hours while removing the benzene and water to form a crude p-vinylphenol polymer consisting of 2.5% oligomers of vinylphenols, 1.9% phenol and m- and p-cresols, 72.5% unreacted ethylphenols, 18.3% p-vinylphenol polymer, 0.5% o-vinylphenol, and 4.3% m-vinylphenol. The crude polymer was pre-heated to about 50° C, and fed into a film evaporator (made of SUS 32 stainless steel; rotor speed 500 rpm; heat transmission area 0.13 m$^2$) at a feed rate of 10 l/hr under a pressure of 3 mmHg while maintaining the heat transfer medium at a temperature of 250° C. The concentrated solution was received as a viscous liquid by a receiver held at 170° to 250° C, whereafter the concentrated solution was taken out of the system and cooled and solidified.

The resulting p-vinylphenol polymer was a purified p-vinylphenol polymer containing 0.1% ethylphenols and o- and m-vinylphenols and 0.9% oligomers of vinylphenols. UV, IR and NMR spectroscopic analyses of this polymer that it was a vinyl polymer of p-vinylphenol. The resulting polymer was found to have a weight average molecular weight of 7,121.

The purified p-vinylphenol polymer obtained is a brittle solid at room temperature and thus lends itself to easy handling. It can be transported in the pulverized condition. It also has an advantage of low hygroscopicity because of its low surface area per unit weight.

EXAMPLE 2

Crude vinylphenol, the same dehydrogenation product as obtained in Example 1, was placed directly into a three necked glass reactor equipped with a stirrer, and heat polymerized at 140° C for 5 hours while removing the benzene and water to obtain a curde p-vinylphenol polymer consisting of 2.7% oligomers of vinylphenols, 1.9% phenol and m- and p-cresols, 72.4% unreacted ethylphenols, 18.2% p-vinylphenol polymer, 0.5% o-vinylphenol, and 4.3% m-vinylphenol. The curde polymer was pre-heated to about 50° C and fed into a film evaporator at a feed rate of 16 l/hr under a pressure of 4 mmHg while maintaining the heat transfer medium at a temperature of 250° C. Otherwise, the conditions were the same as in Example 1. A purified p-vinylphenol polymer having a weight average molecular weight of 4,831 and containing 0.6% ethylphenols and o- and m-vinylphenols and 2.1% oligomers of vinylphenols was obtained almost quantitatively.

The distillate from the film evaporator consisted of 2.9% low molecular weight oligomers of vinylphenols, 2.6% phenol and m- and p-cresols, 91.0% unreacted ethylphenols, 3.4% o- and m-vinylphenols, traces of p-vinylphenol and 0.1% of other unidentifiable components. This led to the confirmation that the p-vinylphenol polymer was well concentrated.

EXAMPLE 3

Crude vinylphenol, the same dehydrogenation product as obtained in Example 1, was placed directly into a three necked glass reactor equipped with a stirrer, and heat polymerized at 200° C for 1 hour while removing the benzene and water to obtain a crude p-vinylphenol polymer consisting of 2.7% oligomers of vinylphenols, 1.9% phenol and m- and p-cresols, 72.3% unreacted ethylphenols, 18.3% p-vinylphenol polymer, 0.5% o-vinylphenol and 4.3% m-vinylphenol. The crude polymer was pre-heated to about 50° C, and fed into a film evaporator at a feed rate of 2.7 l/hr under a pressure of 6 mmHg while maintaining the heat transfer medium at a temperature of 250° C. Otherwise, the conditions were the same as in Example 1. A purified vinylphenol polymer having a weight average molecular weight of 3,281 and containing 0.7% ethylphenols and 3.8% low molecular weight oligomers of vinylphenols was obtained almost quantitatively.

EXAMPLE 4

Crude ethylphenol consisting of 1.1% phenol and m- and p-cresol, 0.7% o-ethylphenol, 5.0% m-ethylphenol and 93.2% p-ethylphenol was dissolved in benzene, and dehyrodgenated at a temperature of 550° C and an LHSV of 1.0 hr$^{-1}$ under atmospheric pressure using the same catalyst as in Example 1, with the molar ratio of ethylphenols/benzene/water being about 1/1/10. The resulting product was allowed to stand at room temperature followed by separating the water. The crude vinylphenol so separated consisted of 33.1% benzene, 1.5% phenol and m- and p-cresols, 0.4% o-ethylphenol, 2.7% m-ethylphenol, 48.1% p-ethylphenol, 0.1% o-vinylphenol, 0.5% m-vinylphenol, 8.9% p-vinylphenol, 0.8% oligomers of vinylphenols and 3.9% water with the vinylphenols/ethylphenols molar ratio being 0.19.

This crude vinylphenol was placed in a three necked glass reactor equipped with a stirrer, and heat polymerized at 140° C for 5 hours while removing the benzene and water to obtain a crude p-vinylpenol polymer consisting of 1.5% oligomers of vinylphenols, 2.3% phenol and m- and p-cresol, 81.2% unreacted ethylphenols, 14.0% p-vinylphenol polymer, 0.2% o-vinylphenol, and 0.8% m-vinylphenol. The crude polymer was pre-heated to about 50° C and fed into a film evaporator at a feed rate of 11 l/hr under a pressure of 6 mmHg while maintaining the heat transfer medium at a temperature of 250° C. Otherwise, the conditions were the same as in Example 1. A purified p-vinylphenol polymer having a weight average molecular weight of 3,300 and containing 1.0% ethylphenols and o- and m-vinylphenols and 1.5% oligomers of vinylphenols was obtained almost quantitatively.

EXAMPLE 5

Crude ethylphenol consisting of 1.1% phenol and m- and p-cresols, 0.1% o-ethylphenol, 0.5% m-ethylphenol and 98.3% p-ethylphenol was dissolved in benzene, and dehydrogenated at a temperature of 600° C and LHSV of 1.0 hr$^{-1}$ under atmospheric pressure using the same catalyst as in Example 1, with the ethylphenol/benzene/water molar ratio being about 1/1/12. The resulting product was allowed to stand at room temperature followed by separating the water. The crude vinylphenol so separated consisted of 40.2% benzene, 6.9% phenol and m- and p-cresols, traces of o-ethylphenol, 0.2% m-ethylphenol, 24.4% p-ethylphenol, traces of o-vinylphenol, 0.2% m-vinylphenol, 22.2% p-vinylphenol, 1.6% oligomers of vinylphenols and 4.3% water with the vinylphenols/ethylphenols molar ratio being 0.93. The crude vinylphenol was directly placed in a three necked glass reactor equipped with a stirrer, and heat polymerized at 140° C for 5 hours while removing the benzene and water to obtain a crude p-vinylphenol polymer consisting of 3.6% oligomers of vinylphenols, 12.2% phenol and m- and p-cresols, 44.3% unreacted ethylphenols, 39.5% p-vinylphenol polymer, a trace of o-vinylphenol and 0.4% m-vinylphenol. The crude polymer was pre-heated to about 50° C, and fed into a film evaporator at a feed rate of 7 l/hr under pressure of 8 mmHg while maintaining the heat transfer medium at a temperature of 270° C. Otherwise, the conditions were the same as in Example 1. A purified p-vinyl-phenol polymer having a weight average molecular weight of 6,524 and containing 0.3% ethylphenols and o- and m-vinylphenol and 1.5% oligomers of vinylphenols was obtained almost quantitatively.

EXAMPLE 6

The crude p-vinylphenol polymer obtained in Example 1 was pre-heated to about 50° C and fed into a film evaporator at a feed rate of 30 l/hr under pressure of 100 mmHg while maintaining the heat transfer medium at a temperature of 250° C. Otherwise, the conditions were the same as in Example 1. The concentrated solution was received as a viscous liquid by a receiver held at 200° C and sealed with $N_2$. A part of the concentrated solution was taken out and analyzed. It was found to consist of 6.3% low molecular weight oligomers of vinylphenols, 83.6% p-vinylphenol polymer, and 10.1% phenols, unreacted ethylphenols and o- and m-vinylphenols. The concentrated solution was again fed into the same type of film evaporator at a feed rate of 15 l/hr under a pressure of 10 mmHg while maintaining the heat transfer medium at a temperature of 270° C. The concentrated solution was received as a viscous liquid by a receiver held at 250° C and sealed with $N_2$. The concentrated solution was taken out of the system, and cooled and solidified. In this manner, a purified p-vinylphenol polymer having a weight average molecular weight of 6,700 and containing 0.3% ethylphenols and 1.5% low molecular weight oligomers of vinylphenols was obtained almost quantitatively.

EXAMPLE 7

The crude p-vinylphenol obtained in Example 5 was directly placed in a three necked glass reactor equipped with a stirrer, and, after the removal of the benzene and water at 50° C and at 60 mmHg, heat polymerized at 50° C for 72 hours to obtain a crude p-vinylphenol polymer consisting of 3.0% oligomers of vinylphenols, 12.5% phenol and m- and p-cresols, 44.4% unreacted ethylphenols, 39.8% p-vinylphenol polymer and 0.3% o- and m-vinylphenols. The crude polymer was pre-heated to about 50° C and fed into a film evaporator at a feed rate of 7 l/hr under a pressure of 10 mmHg while maintaining the heat transfer medium at a temperature of 280° C. Otherwise, the conditions were the same as in Example 1. A purified p-vinylphenol polymer having a weight average molecular weight of 14,000 and containing 1.0% ethylphenols and o- and m-vinylphenols and 1.9% low molecular weight oligomers of vinylphenols was obtained almost quantitatively.

EXAMPLE 8

The crude ethylphenol used in Example 1 (consisting of 2.6% phenol and m- and p-cresols, 1.2% o-ethylphenol, 9.4% m-ethylphenol and 86.8% p-ethylphenol) and the crude vinylphenol obtained in Example 5 were mixed in a weight ratio of 1:1 to form crude vinylphenol consisting of 18.9% benzene, 4.5% phenol and m- and p-cresol, 0.7% o-ethylphenol, 4.5% m-ethylphenol, 55.9% p-ethylphenol, traces of o-vinylphenol, 0.1% m-vinylphenol, 11.3% p-vinylphenol, 1.0% oligomers of vinylphenols and 3.1% water, with the vinylphenols/ethylphenols molar ratio being 0.19. The resulting crude vinylphenol was directly placed in a three necked glass reactor equipped with a stirrer, and heat polymerized at 140° C for 4 hours while removing the benzene and water to obtain a crude p-vinylphenol polymer consisting of 1.5% oligomers of vinylphenols, 6.0% phenol and m- and p-cresols, 78.2% unreacted ethylphenols, 14.2% p-vinylphenol polymer, traces of o-vinylphenol and 0.1% m-vinylphenol. The crude polymer was dropwise added to benzene in an amount of 5 times the weight of the p-vinylphenol polymer in the starting crude polymer. The mixture was vigorously stirred to precipitate and separate at room temperature the p-vinylphenol polymer. The p-vinylphenol polymer so separated contained 27.1% ethylphenols.

This p-vinylphenol polymer was further washed at room temperature six times batchwise with benzene in an amount of 2.5 times the weight of the p-vinylphenol polymer in the original crude p-vinylphenol polymer using a Buchner funnel, and filtered to afford a purified p-vinylphenol polymer having a weight average molecular weight of 3,500 and containing 0.6% ethylphenol and 0.3% oligomers of vinylphenols in a yield of 87.8% (based on the starting crude polymer).

In theory, according to this method, a greater portion of the oligomers is dissolved in the ethylphenols and removed at the stage where the crude p-vinylphenol polymer is dropwise added to a non-solvent for the polymer to precipitate the polymer. At this time, the polymer precipitated becomes very porous. The subsequent washing presumably causes the ethylphenols to be dissolved in the non-solvent and thus removed. The p-vinylphenol polymer so obtained is very porous and is well soluble in a polar solvent, and is substantially white in color.

EXAMPLE 9

The crude p-vinylphenol polymer obtained in Example 8 (consisting of 1.5% oligomers of vinylphenols, 6.0% phenol and m- and p-cresols, 78.2% unreacted ethylphenols, 14.2% p-vinylphenol polymer, traces of o-vinylphenol and 0.1% m-vinylphenol) was dropwise added to benzene in an amount of 10 times the weight of the p-vinylphenol polymer in the starting crude polymer. The mixture was vigorously stirred at room temperature to precipitate and separate the p-vinylphenol polymer. The p-vinylphenol polymer separated contained 24.3% ethylphenols. The polymer was washed five times by the same procedure and under the same conditions as in Example 8. A purified p-vinylphenol polymer having a weight average molecular weight of 3,415 and containing 0.4% ethylphenols and 0.1% oligomers of vinylphenols was obtained in a yield of 91.3%.

EXAMPLE 10

The crude p-vinylphenol polymer obtained in Example 8 was dropwise added to benzene in an amount of 20 times the weight of the p-vinylphenol polymer in the starting crude polymer. The mixture was vigorously stirred at room temperature to precipitate and separate the p-vinylphenol polymer. The p-vinylphenol polymer so separated contained 18.5% ethylphenols. The polymer was then washed at room temperature four times by the same procedure and under the same conditions as in Example 8. A purified p-vinylphenol polymer having a weight average molecular weight of 3,620 and containing 0.5% ethylphenols and 0.2% oligomers of vinylphenols was obtained in a yield of 100%.

EXAMPLE 11

The crude p-vinylphenol polymer obtained in Example 8 was dropwise added to benzene to an amount of 20 times the weight of the p-vinylphenol polymer in the starting crude polymer. The mixture was vigorously stirred at room temperature to precipitate and separate the p-vinylphenol polymer. The p-vinylphenol polymer so separated contained 16.5% ethylphenols. The polymer was then continuously washed at room temperature with benzene in an amount of 5 times the weight of the p-vinylphenol polymer in the starting crude polymer using a pressure filter (1 kg/cm$^2$; pressurized with $N_2$ gas) to afford a purified p-vinylphenol polymer having a weight average molecular weight of 3,510 and containing 0.2% ethylphenols and traces of oligomers of vinylphenols in a yield of 100%.

EXAMPLE 12

The crude p-vinylphenol polymer obtained in Example 8 was dropwise added to toluene in an amount of 20 times the weight of the p-vinylphenol polymer in the starting crude polymer. The mixture was vigorously stirred at room temperature to precipitate and separate the p-vinylphenol polymer. The p-vinylphenol polymer so separated contained 17.5% ethylphenols. The polymer was then washed at room temperature four times by the same procedure and under the same conditions as in Example 8 to afford a purified p-vinylphenol polymer having a weight average molecular weight of 3,515 and containing 0.7% ethylphenols and 0.2% oligomers of vinylphenols in a yield of 100%.

EXAMPLE 13

Crude ethylphenol consisting of 2.0% phenol and m- and p-cresols, 0.2% o-ethylphenol, 55.8% m-ethylphenol and 42.0% p-ethylphenol was dissolved in benzene, and dehydrogenated at a temperature of 600° C and LHSV of 1.0 hr$^{-1}$ under atmospheric pressure using the same catalyst as in Example 1, with the ethylphenol/benzene/water molar ratio being 1/1/12. The resulting product was allowed to stand at room temperature followed by separating the water. The crude vinylphenol so separated consisted of 39.0% benzene, 4.3% phenol and m- and p-cresols, 0.1% o-ethylphenol, 22.1% m-ethylphenol, 10.4% p-ethylphenol, traces of o-vinylphenol, 10.1% m-vinylphenol, 9.5% p-vinylphenol, 0.5% oligomersof vinylphenols and 4.0% water with the p-vinylphenol/(ethylphenols + m-vinylphenol) molar ratio being 0.61. The crude vinylphenol was directly placed in a three necked glass reactor equipped with a stirrer, and heat polymerized at 140° C for 4 hours to afford a crude p-vinylphenol polymer consisting of 1.2% oligomers of vinylphenols, 7.5% phenol and m- and p-cresols, 0.2% o-ethylphenol, 39.0% m-ethylphenol, 18.3% p-ethylphenol, 17.4% m-vinylphenol, and 16.4% p-vinylphenol polymer.

When this crude polymer was purified in the same way as in Example 10, a purified p-vinylphenol polymer having a weight average molecular weight of 3,500 and containing 0.5% ethylphenols and 0.2% oligomers of vinylphenols was obtained in a yield of 100%.

EXAMPLE 14

The crude p-vinylphenol obtained in Example 5 was thoroughly dried with Glauber's salt, and, after adding 3 mol%, based on the p-vinylphenol, of $BF_3$ etherate, polymerized for 30 minutes at 5° to 10° C with stirring. The p-vinylphenol polymer precipitated was separated by filtration, and washed at room temperature six times batchwise with benzene in an amount of 25 times the weight of the p-vinylphenol polymer using a Buchner funnel. A 0.01 N aqueous solution of hydrochloric acid was then added in an amount of 20 times the weight of the p-vinylphenol polymer, and the mixture was stirred at room temperature for 1 hour. The polymer was separated by filtration, washed at room temperature and filtered six times with the same amount of water as the hydrochloric acid aqueous solution, and dried. A purified p-vinylphenol polymer having a weight average molecular weight of 8,600 and containing 0.8% phenols and other impurities was obtained in a yield of 99% based on the starting crude polymer.

While the invention has been described in detail and with reference to specific embodiments thereof, it will be apparent to one skilled in the art that various changes and modifications can be made therein without departing from the spirit and scope thereof.

What is claimed is:

1. A process for preparing a p-vinylphenol polymer which comprises dehydrogenating crude p-ethylphenol containing at least one of m-ethylphenol and o-ethylphenol to convert the ethylphenol(s) to vinylphenol(s), polymerizing the resulting crude product by heat or cationic polymerization without purification, and then purifying the resulting polymerization product by precipitating the p-vinylphenol with a non-solvent therefor or by the film evaporation method.

2. The process of claim 1, wherein the total amount of the m- and o-ethylphenol isomers in the crude p-ethylphenol is not more than about 95 parts by weight per about 5 parts by weight of the p-ethylphenol.

3. The process of claim 1, wherein the total amount of the m- and o-ethylphenol isomers in the crude p-ethylphenol is not more than about 50 parts by weight per about 50 parts by weight of the p-ethylphenol.

4. The process of claim 1, wherein the crude p-ethylphenol is a reaction product obtained by sulfonating ethylbenzene with sulfuric acid and subjecting the sulfonation product to alkali fusion.

5. The process of claim 1, wherein the crude p-ethylphenol is a reaction product obtained by sulfonating ethylbenzene with sulfuric acid, separating the p-isomer of the sulfonated ethylbenzene by crystallizing and subjecting the p-isomer of the sulfonated ethylbenzene to alkali fusion.

6. The process of claim 1, wherein the crude p-ethylphenol is a product obtained by sulfonating ethylbenzene with sulfuric acid and subjecting the sulfonation product to alkali fusion, and subjecting the resulting product to simple distillation to remove compounds having a boiling point of not more than about 200° C.

7. The process of claim 6, wherein the compounds having a boiling point of not more than about 200° C are cresol and phenol.

8. The process of claim 1, wherein the crude p-ethylphenol has been distilled to remove the o-ethylphenol prior to the dehydrogenation.

9. The process of claim 1, wherein the crude p- ethylphenol consists of about 64 to about 90.5% by weight of p-ethylphenol and about 4 to about 10% by weight of m-ethylphenol and/or about 4 to about 10% by weight of o-ethylphenol.

10. The process of claim 1, wherein the crude p-ethylphenol consists of about 90 to about 98% by weight of p-ethylphenol and about 0.4 to about 1% by weight of o-ethylphenol and/or about 0.4 to about 1% by weight of m-ethylphenol.

11. The process of claim 1, wherein the crude p-ethylphenol consists of about 98 to about 99.5% by weight of p-ehtylphenol, about 0.1 to about 0.2% by weight of o-ethylphenol and about 0.4 to about 1% by weight of m-ethylphenol.

12. The process of claim 1, wherein the dehydrogenation is carried out by heating the crude p-ethylphenol in the presence of a metal oxide catalyst.

13. The process of claim 12, wherein the dehydrogenation is carried out at about 400° to about 700° C.

14. The process of claim 13, wherein the dehydrogenation is carried out in the presence of an organic diluent.

15. The process of claim 1, wherein the dehydrogenation is carried out until the conversion becomes about 20 to about 70%.

16. The process of claim 1, wherein the heat polymerization is carried out at a temperature of about 50° to about 200° C using about 0.05 to about 100 mols of a diluent per mol of the p-vinylphenol.

17. The process of claim 16, wherein the diluent is crude p-ethylphenol.

18. The process of claim 1, wherein the polymerization is carried out at a temperature of about 30° to about 80° C using a halide of boron, antimony, iron, tellurium, tin, titanium, bismuth or zinc, sulfuric acid, hydrofluoric acid, phosphoric acid, phosphorus pentoxide, or hydrochloric acid as a catalyst and 0 to about 1,000% by weight of a diluent.

* * * * *